US009707050B2

(12) United States Patent
Guaragno et al.

(10) Patent No.: US 9,707,050 B2
(45) Date of Patent: Jul. 18, 2017

(54) DENTAL HANDPIECE

(71) Applicant: DENTSPLY INTERNATIONAL INC., York, PA (US)

(72) Inventors: Kenneth R. Guaragno, Spring Grove, PA (US); Jared Witmer, Lewisberry, PA (US); Clive Swatton, Mount Joy, PA (US)

(73) Assignee: Dentsply Sirona Inc., York, PA (US)

( * ) Notice: Subject to any disclaimer, the term of this patent is extended or adjusted under 35 U.S.C. 154(b) by 107 days.

(21) Appl. No.: 14/716,075

(22) Filed: May 19, 2015

(65) Prior Publication Data

US 2015/0327951 A1 Nov. 19, 2015

Related U.S. Application Data

(60) Provisional application No. 62/000,145, filed on May 19, 2014.

(51) Int. Cl.
| | |
|---|---|
| *A61C 1/07* | (2006.01) |
| *A61C 19/00* | (2006.01) |
| *A61C 17/00* | (2006.01) |
| *A61C 1/16* | (2006.01) |
| *A61C 17/20* | (2006.01) |
| *A61C 1/18* | (2006.01) |

(52) U.S. Cl.
CPC ............... *A61C 1/07* (2013.01); *A61C 1/16* (2013.01); *A61C 1/188* (2013.01); *A61C 17/005* (2013.01); *A61C 17/20* (2013.01); *A61C 19/002* (2013.01)

(58) Field of Classification Search
CPC .. A61C 17/20; A61C 1/07; A61C 1/16; A61C 1/188; A61C 19/002; A61C 17/005
See application file for complete search history.

(56) References Cited

U.S. PATENT DOCUMENTS

| | | | |
|---|---|---|---|
| 1,992,770 | A | 2/1935 | Rathbun |
| 2,344,605 | A | 3/1944 | Droegkamp |
| 3,178,951 | A | 4/1965 | Ulbing |
| 3,654,502 | A | 4/1972 | Carmona et al. |
| 3,921,044 | A | 11/1975 | McShirley |
| 3,956,826 | A | 5/1976 | Perdreaux, Jr. |

(Continued)

FOREIGN PATENT DOCUMENTS

| | | |
|---|---|---|
| DE | 10334467 B4 | 3/2009 |
| EP | 1180350 A1 | 2/2002 |

(Continued)

*Primary Examiner* — Glenn Richman
(74) *Attorney, Agent, or Firm* — McNees Wallace & Nurick LLC

(57) ABSTRACT

A dental handpiece and a dental cleaning procedure are disclosed. The dental handpiece includes an inner barrel for rotatably retaining an ultrasonic insert, the inner barrel configured for contacting the ultrasonic insert with a cooling fluid in the inner barrel, a coil unit arranged and disposed to apply an alternating magnetic field to the ultrasonic insert when positioned in the inner barrel, an outer sheath extending around at least a portion of the coil unit. The dental handpiece includes flow regions permitting steam, chemicals, and heat to flow into the inner barrel and out of the inner barrel during a sterilization technique. The dental cleaning procedure includes operating the dental handpiece and autoclaving the dental handpiece.

20 Claims, 7 Drawing Sheets

(56) References Cited

U.S. PATENT DOCUMENTS

| | | | |
|---|---|---|---|
| 4,110,908 A | 9/1978 | Cranston | |
| RE30,536 E | 3/1981 | Perdreaux, Jr. | |
| 4,534,734 A | 8/1985 | Lares | |
| 4,741,731 A | 5/1988 | Starck et al. | |
| 5,382,162 A | 1/1995 | Sharp | |
| 5,395,240 A | 3/1995 | Paschke et al. | |
| 5,501,596 A | 3/1996 | Bailey | |
| 5,655,906 A | 8/1997 | Coss et al. | |
| 5,743,718 A | 4/1998 | Mendoza et al. | |
| 6,012,922 A | 1/2000 | Novak | |
| 6,186,789 B1 | 2/2001 | Hugo et al. | |
| 6,416,525 B1 | 7/2002 | Shibata | |
| 6,623,500 B1 | 9/2003 | Cook et al. | |
| 6,716,028 B2* | 4/2004 | Rahman | A61C 17/20 433/119 |
| 6,811,399 B2 | 11/2004 | Rahman et al. | |
| 7,011,520 B2 | 3/2006 | Rahman et al. | |
| 7,217,128 B2 | 5/2007 | Atkin et al. | |
| 7,530,809 B2 | 5/2009 | Atkin et al. | |
| 8,435,034 B2* | 5/2013 | Gersh | A61C 17/20 433/119 |
| 8,678,820 B2* | 3/2014 | Jamnia | A61B 17/32006 433/119 |
| 8,961,176 B2* | 2/2015 | Paschke | A61C 1/07 433/117 |
| 9,050,161 B2* | 6/2015 | Feine | A61C 1/0015 |
| 2002/0127512 A1 | 9/2002 | Chen et al. | |
| 2003/0022129 A1 | 1/2003 | Rahman et al. | |
| 2003/0108844 A1 | 6/2003 | Rahman et al. | |
| 2004/0126738 A1 | 7/2004 | Atkin et al. | |
| 2004/0191724 A1 | 9/2004 | Rahman et al. | |
| 2004/0265776 A1 | 12/2004 | Tipton et al. | |
| 2005/0266377 A1 | 12/2005 | Tsao | |
| 2006/0068361 A1 | 3/2006 | Bergler et al. | |
| 2008/0044790 A1 | 2/2008 | Fani et al. | |
| 2008/0057470 A1 | 3/2008 | Levy et al. | |
| 2010/0008712 A1 | 1/2010 | Sitz et al. | |
| 2011/0033823 A1 | 2/2011 | Gersh et al. | |
| 2011/0177474 A1* | 7/2011 | Jamnia | A61B 17/32006 433/119 |
| 2011/0250559 A1 | 10/2011 | Feine | |

FOREIGN PATENT DOCUMENTS

| | | |
|---|---|---|
| EP | 1279380 A1 | 1/2003 |
| JP | 2002113020 | 4/2002 |
| WO | 02069315 A2 | 9/2002 |
| WO | 2004/052230 A1 | 6/2004 |
| WO | 2008-83366 A2 | 7/2008 |
| WO | 2008113001 A1 | 9/2008 |
| WO | 2009116994 A1 | 9/2009 |

* cited by examiner

DENTAL HANDPIECE

CROSS-REFERENCE TO RELATED APPLICATIONS

The present invention is a non-provisional patent application claiming priority and benefit of U.S. Provisional Patent Application No. 62/000,145, titled "Dental Medical Handpiece Having a Rotatable Inner Chamber," filed May 19, 2014, the entirety of which is incorporated by reference.

FIELD OF THE INVENTION

The present invention is generally dental medical handpieces, dental medical systems including dental medical handpieces, and processes of using dental medical handpieces. More particularly, the present invention is related to such systems, handpieces, and processes relying upon ultrasonics.

BACKGROUND OF THE INVENTION

An ultrasonic dental tool typically includes a handpiece connected to a cable that has lavage and connects electrical power, ground, and feedback circuits. The cable may include a flexible tube to provide the lavage (for example, water chlorohexidine, and/or mouth wash). The cable connects a scaling unit to the handpiece circuits.

During a typical ultrasonic cleaning procedure, a dentist or hygienist will need to change the direction of an insert tip relative to the lay of the cable in the dental tool in order to properly adapt to the tooth surface being cleaned. Because the insert to handpiece seal is a static seal, it is not easily rotated because of frictional forces (from having a tight fit). Typically, the insert must be removed from a patient's mouth and both hands of the dentist or the hygienist must be used to rotate the tip (for example, moving from mandibular anterior to maxillary premolar). Such action interrupts workflow and, thus, productivity. Without changing the orientation of the tip, the dentist or the hygienist would have to counter the cable's torsional load on the handpiece in order to maintain proper tip angulation, which results in a higher pinch grip force. Tighter pinch grips can be a source of fatigue, reduction in tactile sensitivity, and/or the ability to assure patient comfort.

A dental medical handpiece, dental medical system including a dental medical handpiece, and a process of using a dental medical handpiece that show one or more improvements in comparison to the prior art would be desirable in the art.

BRIEF DESCRIPTION OF THE INVENTION

In an embodiment, a dental handpiece includes an inner barrel for rotatably retaining an ultrasonic insert, the inner barrel configured for contacting the ultrasonic insert with a cooling fluid in the inner barrel, a coil unit arranged and disposed to apply an alternating magnetic field to the ultrasonic insert when positioned in the inner barrel, and an outer sheath extending around at least a portion of the coil unit. The dental handpiece includes flow regions permitting steam, chemicals, and heat to flow into the inner barrel and out of the inner barrel during a sterilization technique.

In another embodiment, a dental handpiece includes an inner barrel for rotatably retaining an ultrasonic insert, the inner barrel configured for contacting the ultrasonic insert with a cooling fluid in the inner barrel, a coil unit arranged and disposed to apply an alternating magnetic field to the ultrasonic insert when positioned in the inner barrel, and an outer sheath extending around at least a portion of the coil unit. The dental handpiece is configured for adjusting torque from a lower torque level to a higher torque level by adjustment of a swivel drag adjustment screw.

In another embodiment, a dental cleaning procedure includes operating a dental handpiece thereby applying an alternating magnetic field to an ultrasonic insert positioned in an inner barrel of the dental handpiece, and autoclaving the dental handpiece, allowing steam to flow through flow regions in the dental handpiece.

Other features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Provided is a dental handpiece. Embodiments of the present disclosure, for example, in comparison to concepts failing to include one or more of the features disclosed herein, permit exposure to an increased number of sterilization cycles, permit exposure to an increased range of temperature cycles, allow use of autoclaving techniques not previously practicable, reduce or eliminate short-circuits, permit more dentists and hygienists to be more productive, permit more dentists and hygienists to avoid fatigue and injury, generate other suitable advantages that will be apparent from the present disclosure, or a combination thereof.

Figure 1:
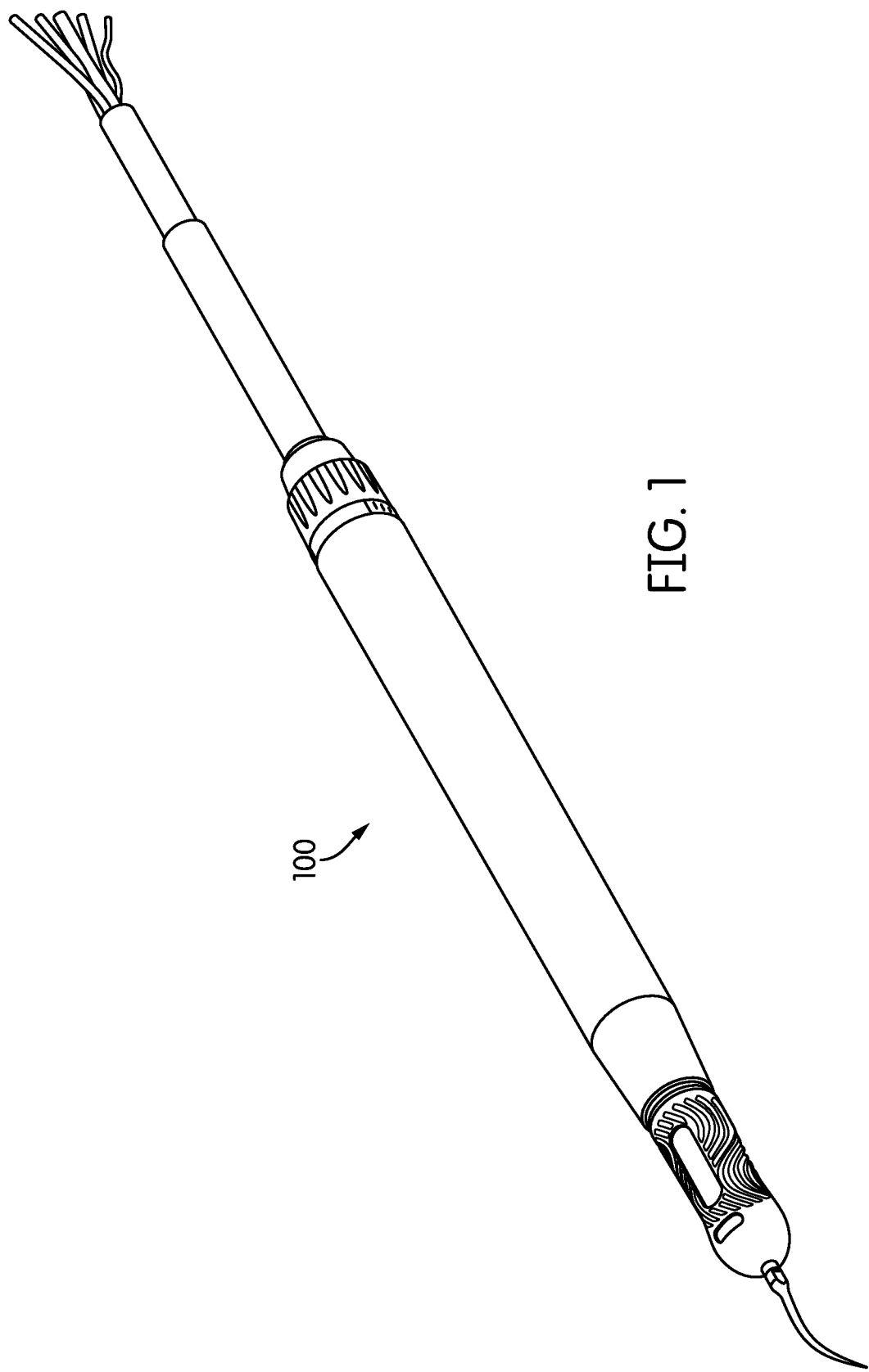
FIG. 1 shows a perspective view of a dental handpiece in assembled form, according to an embodiment of the disclosure.
Figure 2:
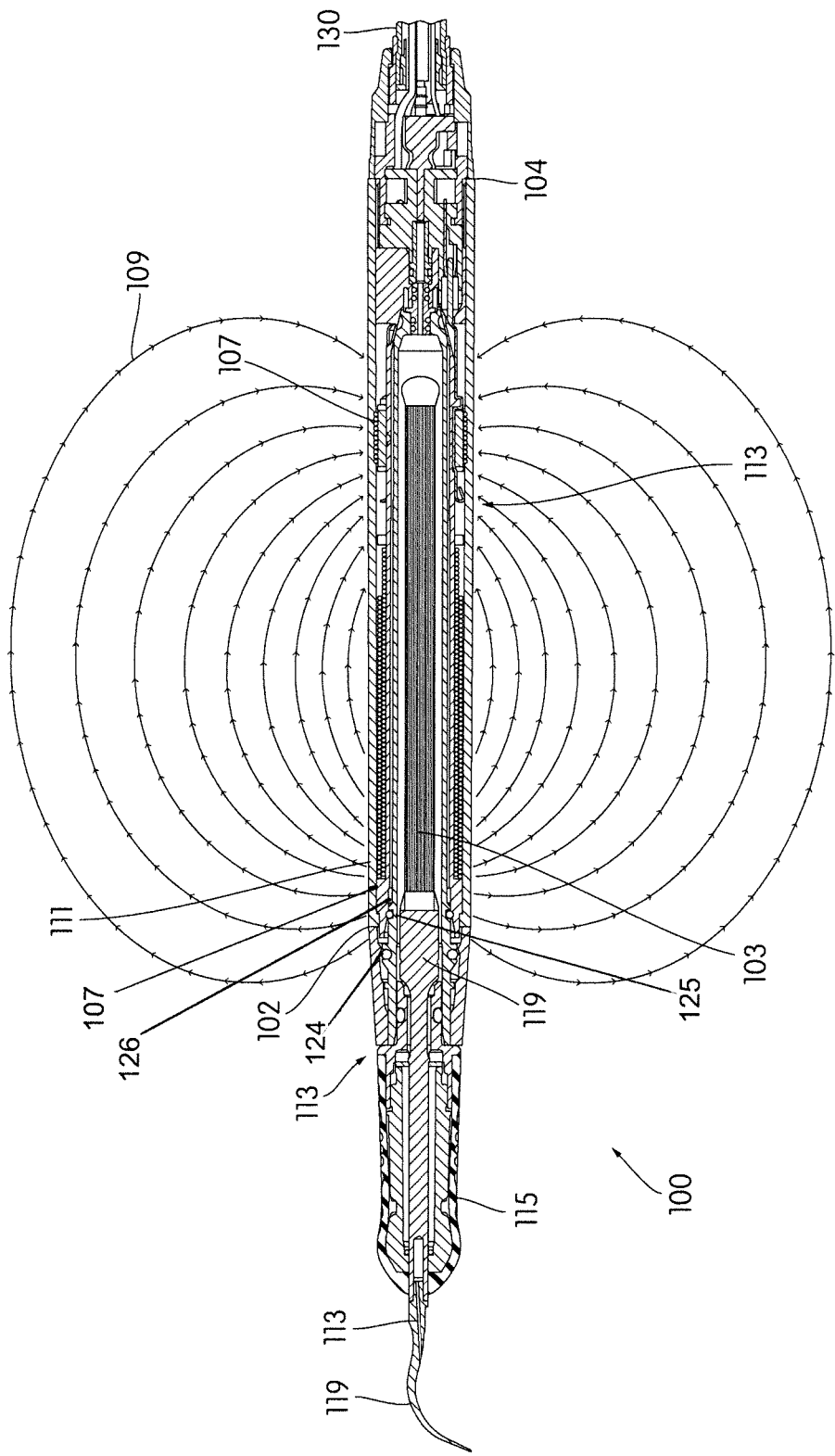
FIG. 2 shows a section view of a dental handpiece in assembled form, according to an embodiment of the disclosure.
Figure 3:
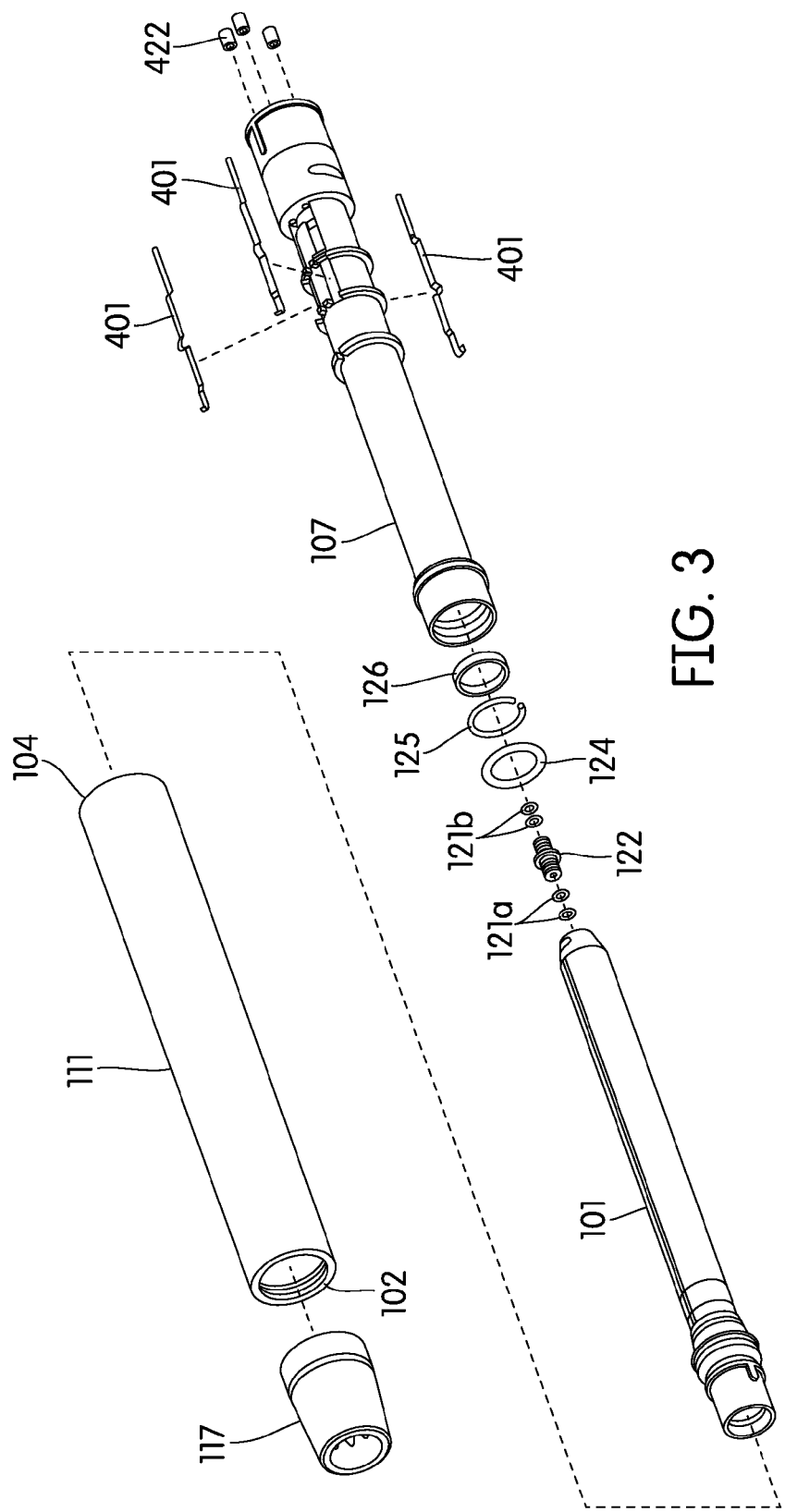
FIG. 3 is a perspective view of a dental handpiece in disassembled form, according to an embodiment of the disclosure.

FIG. 1 shows a dental handpiece 100 capable of being used for supra and sub-gingival treatment, periodontal debridement, endodontic procedures, or other oral procedures. Referring to FIGS. 2-3, the dental handpiece 100 includes an inner sheath, or barrel, 101 for rotatably retaining an ultrasonic insert 103 (for example, allowing 360 degree rotation of the ultrasonic insert 103). The inner barrel 101 is configured for contacting the ultrasonic insert 103 with a cooling fluid 105 in the inner barrel 101. The dental handpiece 100 further includes a coil unit 107 arranged and disposed to apply an alternating magnetic field 109 to the ultrasonic insert 103 when positioned in the inner barrel 101, and an outer sheath 111 extending around at least a portion of the coil unit 107. The dental handpiece 100 includes flow regions 113 permitting steam, chemicals, and heat to flow into the inner barrel 101 and out of the inner barrel 101 during a sterilization technique.

The material for the elements of the dental handpiece 100 includes any suitable material capable of withstanding temperature and pressure of autoclaving. Such conditions are those that apply to using steam autoclaves, chemical vapor autoclaving, rapid dry heating, transfer sterilization, dry heating, and/or ultrasonic cleaning, for example, at an operating temperature of 132° C. to 190° C. for 10 to 30 minutes wrapped, followed by 3 to 6 minutes unwrapped, in the presence of chemicals such as formaldehyde and/or alcohol, and/or under cooling/drying conditions for 10-20 minutes. Suitable materials include, but are not limited to, polyetherimide, glass-fiber reinforced materials, amorphous polyamide resin, and/or liquid crystal polymer material.

The outer sheath 111 protects users of the dental handpiece 100 (such as, a dentist or hygienist) as well as those receiving treatment (such as patients), for example, by preventing exposure to electrical contacts and coils, reducing or eliminating biological materials that can lead to infection, and by including surfaces and profiles that allow disinfectant wiping. Additionally, the outer sheath 111 permits ergonomic use of the dental handpiece 100. In general, the outer sheath is tubular and/or cylindrical, with an open interior. The outer sheath 111 includes a larger open end 104 distal from a rotatable nozzle 115 and a smaller open end 102 proximal to the rotatable nozzle 115. In one embodiment, the larger open end 104 is capable of connection/separation from an external cable assembly 130 using securing mechanism 121, such as, tabs and grooves within the outer sheath 111. Other suitable securing mechanisms 121 capable of being utilized within the dental handpiece 100 include, but are not limited to, seals (for example, one or more dynamic seals 201), swivel bearing 126, clips, snap rings or retainers 125, retention coupler 124, and other features that permit disassembly of the dental handpiece 100, features that facilitate removal of debris within the dental handpiece 100, or a combination thereof.

Figure 11:
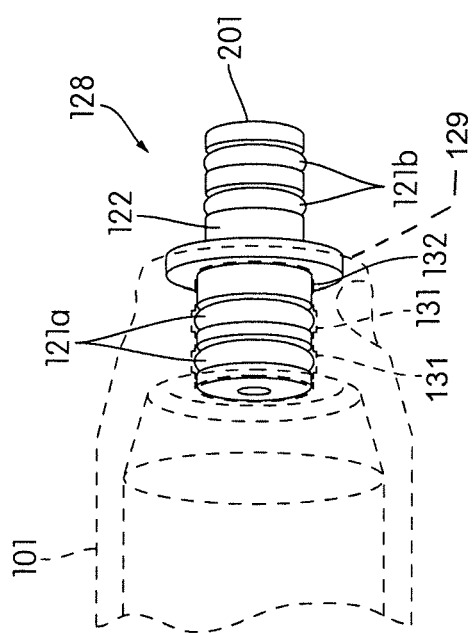
FIG. 11 is an enlarged view of the seal carrier.
Figure 12:
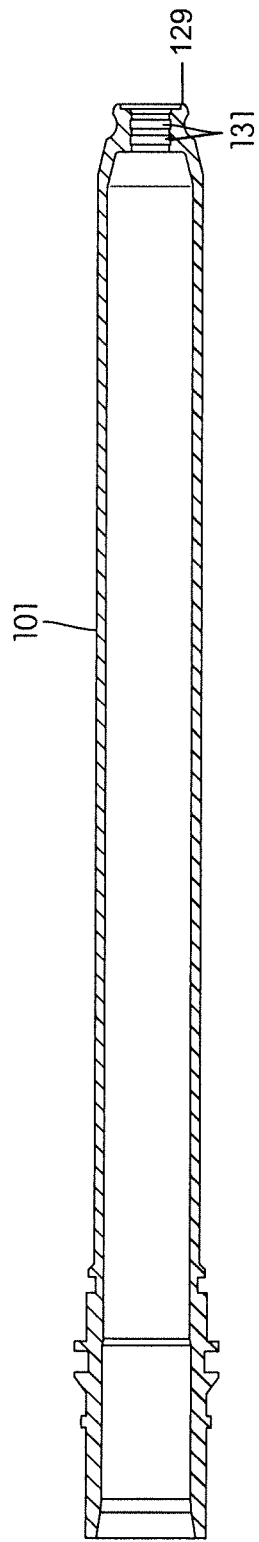
FIG. 12 is a cross-sectional view of the inner sheath.

In one embodiment shown in FIG. 11, the dynamic seal 201 may include a dynamic seal assembly 128 made of one or more compliant members, e.g., an o-ring or a lip seal, arranged on a seal carrier 122. Seal carrier may be, e.g., a machined or molded component, or the like. Seal carrier 122 may be manufactured to have a low friction high integrity surface free of defects, such that the seals 121 can rotate over the seal carrier 122 with little to no friction and resultant wear. Seal carrier 122 can be made of any suitable compliant material, e.g., Teflon®, so that small degrees of misalignment or side loading can be absorbed and not transferred in the seals due to uneven loading and potential loss of compression that may result in leakage. FIG. 12 shows a cross-sectional view of the inner barrel 101. Inner barrel 101 may include receiving grooves 131 for receiving seals 121, e.g., o-rings. Grooves 131 allow the seal assembly 128 to fit precisely in an axial position with the end 129 of inner barrel 101. Grooves 131 create a static seal, i.e., non-rotational seal, between inner barrel 101 and coil unit 107 while maintaining the integrity of the seal 121 to prevent fluid passage. A flange 132 may be provided on seal carrier 122 between static seal o-rings 121a and dynamic seal o-rings 121b, to provide a mechanical stop to aid in alignment of seal carrier 122 in inner barrel 101.

In an embodiment including one of the dynamic seals 201 positioned proximal to the smaller open end 102, the dynamic seal 201 has a diameter that is ⅓ or less in length in comparison to the diameter of the outer sheath 111, thereby reducing friction between the dynamic seal 201 and rotating surface of the dental handpiece 100, allowing for less drag during operation of the dental handpiece 100, allowing for smoother operation of the dental handpiece 100, and/or allowing for operation with torque of less than 1 inch-ounces (in-oz), or ½ in-oz, or 0.01 in-oz, with torque being defined by the following equation:

$$\text{Torque} = \mu R_S R_L, \quad \text{(Equation 1)}$$

Figure 10:
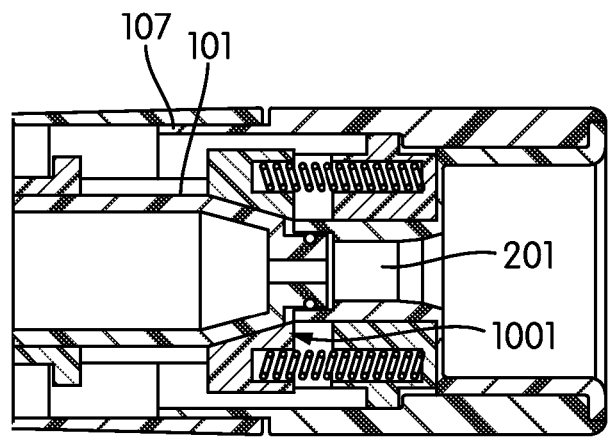
FIG. 10 is a side view of an embodiment of a dental handpiece having a dampener, according to the disclosure.

According to the above equation, $\mu$ refers to the coefficient of friction for the dynamic seal 201, $R_S$ refers to the radius of the seal carrier 122, and $R_L$ refers to axial loading. Referring to FIG. 10, in one embodiment, the dental handpiece 100 includes a dampener 1001 extending around the coil unit 107 for balancing/equalizing pressure on the dynamic seal 201.

In one embodiment, the outer sheath 111 has limited or no crevices that permit bacteria or other biological materials to grow. For example, in one embodiment, the dental handpiece 100 is manufactured such that crevices exist only in flow regions 113, such as, in the larger open end 104 of the dental handpiece 100 distal from the rotatable nozzle 115. In a further embodiment, the flow regions 113 are formed by ribs or by a loose abutting fit between elements of the dental handpiece 100. The flow regions 113 have any suitable dimensions. In one embodiment, the flow regions 113 are between 0.01 mm and 0.5 mm, between 0.02 mm and 0.35 mm, at about 0.25 mm, or any suitable combination, sub-combination, range, or sub-range therein. In a further embodiment, the flow regions 113 include at least two separate paths from outside of the dental handpiece 100 to the interior of the dental handpiece 100.

In embodiments including materials having different coefficients of thermal expansion, crevices defining the flow regions 113 provide sterilization passageways or openings, allowing fluid and heat into the interior of dental handpiece 100 in order to sterilize the inner workings of the handpiece. In one embodiment, the outer sheath 111 has a first coefficient of thermal expansion and the coil unit 107 has a second coefficient of thermal expansion, the first coefficient of thermal expansion differing from the second coefficient of thermal expansion (CTE). Some examples of CTEs are as follows:

For coil form material: Glass fibre reinforced engineering thermoplastic material based on a combination of semicrystallinepPolyamide with partially aromatic copolyamide.

| | |
|---|---|
| 23.0-55.0° C. | |
| Coefficient of Thermal Expansion (Parallel) | 9.00E–05/° K |
| Coefficient of Thermal Expansion (Normal) | 1.50E–05/° K |
| Coil: Copper | |
| 20.0-100° C. | 16.4 μm/° K |

In a further embodiment, the difference between the coefficients of thermal expansion is above a "fracture value," the "fracture value" being a point where fixed/adhesive coupling would have damaged one or both of the outer sheath 111 and the coil unit 107 during the flow of fluid and/or heat during the sterilization technique, for example, by cracking or fracturing the outer sheath 111. In this embodiment, the outer sheath 111 and the coil unit 107 are not damaged during the flow of the fluid and/or the heat during the sterilization technique, despite such a difference between the coefficients thermal expansion being above the fracture value.

The outer sheath 111 extends around coil unit 107, and the coil unit 107 extends around the inner barrel 101. The inner barrel 101 forms a seal with the coil unit 107 abutting one or more of the securing mechanisms 121, such as, o-rings, or dynamic seals. In one embodiment, proximal to the larger open end 104 of the outer sheath 111, the securing mechanism 121 is a dynamic seal that creates a lower amount of drag on ultrasonic insert 103 in comparison to draft on other elements from other seals within the dental handpiece 100. The dynamic seal permits the cooling fluid 105 to flow from being proximal to the larger open end 104 to being proximal to the smaller open end 102, while within the ultrasonic insert 103, prior to cooling and exiting a scaler 119 (such as, a 30 kHz magnetorestrictive scaler) positioned within the rotatable nozzle 115.

Figure 9:
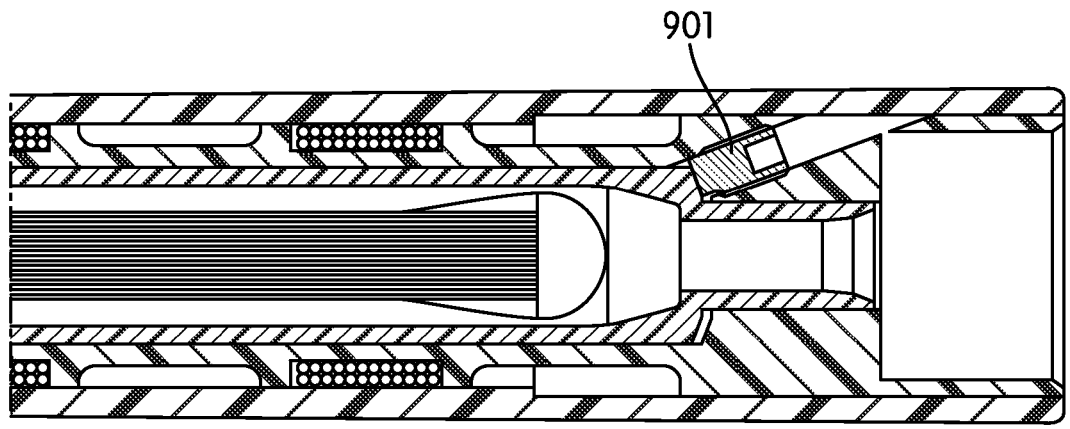
FIG. 9 is a side view of an embodiment of a dental handpiece having a swivel drag adjustment screw, according to the disclosure.

The rotatable nozzle 115 extends from the inner barrel 101, for example, through a grip region 117. The grip region 117 includes a material, such as, an elastomeric material, for handling by the user. In one embodiment, the scaler 119 and/or the ultrasonic insert 103 is/are selectively rotatable, capable of being locked in a fixed position, configured for operation at different torque levels (for example, at a lower torque level and a higher torque level), or a combination thereof in response to application of a force (such as a torsional load) to the grip region 117. Alternatively, other suitable dental devices are included instead of the scaler 119. Referring to FIG. 9, in one embodiment, the torque is adjusted from the lower torque level to the higher torque level by rotating a swivel drag adjustment screw 901 positioned to extend from within the dental handpiece 100 to outside of the dental handpiece 100 where it is adjustable by the dentist or the hygienist. Other suitable mechanisms for torque adjustment include knobs (for example, extending around the outer sheath 111), buttons, clutch assemblies, preloaded barrels, and/or combinations of large and fine adjustment knobs.

Figure 4:
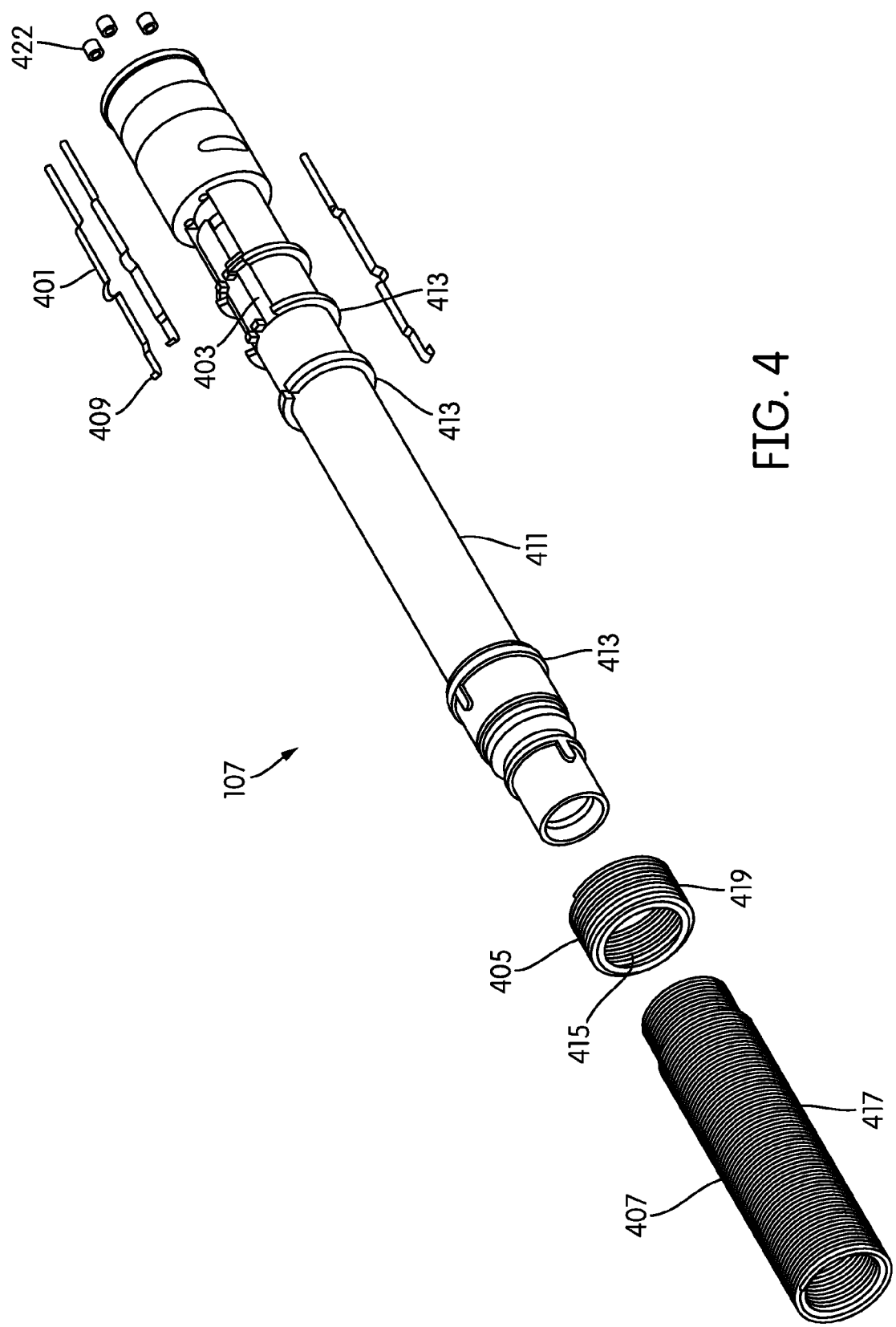
FIG. 4 is a perspective view of a coil unit for an embodiment of a dental handpiece in disassembled form, according to the disclosure.

The coil unit 107 is within the outer sheath 111 of the dental handpiece 100, for example, being movably secured therein. As shown in FIG. 4, in one embodiment, the coil unit 107 is capable of being secured within the outer sheath 111 by having alignment members and/or one or more retaining elements, e.g., coupling pins 401; one or more alignment regions, e.g., as channels 403 corresponding with the coupling pins 401. Coupling pins 401 may provide electrical contacts for the cable assembly 130. Interfacial seals 422 may be provided to provide a fluid seal between the outer sheath 111 and the cable assembly 130. Interfacial seals 422 have an annular opening for receiving one end of a coupling pin 401. Coil unit may also include one or more mating sockets in the cable assembly 130, flanges, molded receptacles, other suitable alignment devices, or a combination thereof.

The coil unit 107 generates the magnetic field 109 that oscillates the ultrasonic insert 103 and, thus, the scaler 119. In one embodiment, the coil unit 107 includes a coated coil wire 123 to extend around the ultrasonic insert 103 (or the region where the ultrasonic insert 103 is to be positioned). The coating reduces or eliminates shorting of the coil unit 107 during the generation of the magnetic field 109.

The coil unit 107 includes other suitable elements, such as a bucking/feedback coil 405 extending from a drive coil 407 in electrical communication with electrical contacts 409, which are capable of being the coupling pins 401. The bucking/feedback coil 405 and the drive coil 407 conduct electricity from an alternating current source that generates the magnetic field 109. The bucking/feedback coil 405 and/or the drive coil 407 are secured to a coil form 411 which serves as a base structure for the coil unit 107, for example, between flanges 413. Wires within the bucking/feedback coil 405 and/or the drive coil 407 are connected to terminals (not shown), provide power, register feedback, and act as a common ground.

A feedback portion of the bucking/feedback coil 405 includes a first wire 415 having a gauge that is smaller than a second wire 417 in the drive coil 407 to register voltage developed by movement of, for example, the ultrasonic insert 103. In one embodiment, the first wire 415 is wound in five layers beginning on a polytetrafluoroethylene tape which is directly against the coil form 411 between the flanges 413 and is connected to a ground terminal and feedback terminal (not shown). In one embodiment, the first wire 415 is polytetrafluoroethylene-coated copper wire with 0.0007 to 0.0011 inch thick insulation on 38 gauge wire.

A bucking portion of the bucking/feedback coil 405 includes a third wire 419, for example, wound in one layer, over the feedback portion of the bucking/feedback coil 405. In one embodiment, the third wire 419 is polytetrafluoroethylene-coated copper wire with 0.0020 to 0.0029 inch thick insulation on 22 gauge wire. The bucking portion reduces or eliminates transformer coupling between the drive coil 407 and the feedback portion of the bucking/feedback coil 405. The bucking portion of the bucking/feedback coil 405 and the drive coil 407 are connected between terminals and in one continuous wire.

The drive coil 407 is attached to the terminal using a right-hand turn, for example, being wound from the flange 413 to the flange 413 and back. The second wire 417 from the drive coil 407 then traverses space between the flanges 413 using a left-hand turn, being wound between the flanges 413 to connect to the bucking portion of the bucking/feedback coil 405. In one embodiment, the second wire 417 is the same, or substantially the same, in size and/or design as the third wire 419.

The bucking portion of the bucking/feedback coil 405 and the drive coil 407 are wired in series and in opposite directions, resulting in being electromagnetically 180° out of phase. The bucking portion of the bucking/feedback coil 405 is electrically insulated from the feedback portion of the bucking/feedback coil 405.

In one embodiment, interposed between all winding layers of the feedback portion and the bucking portion of the bucking/feedback coil 405 is a layer of polytetrafluoroethylene tape (not shown), for example, at about 0.002 inches in thickness. The polytetrafluoroethylene tape is capable of being positioned on polyester and/or polyamide-imide insulation on copper wires. In one embodiment, the polytetrafluoroethylene tape is also used between the layers of the drive coil 407.

The polytetrafluoroethylene tape and/or the polytetrafluoroethylene-coating increases interlayer insulation, which prolongs the life and the number of autoclaving cycles the dental handpiece 100 is capable of experiencing prior to any shorting. In general, the polytetrafluoroethylene is conformable, chemically inert, nonporous, withstands a continuous cycle of temperature from 0° C. to at least 205° C., has high and low temperature stability, has excellent electrical properties, and has good adhesion to copper conductors. Alternatively, in other embodiments, one or more of the elements of the coil unit 107 are devoid of the polytetrafluroethylene tape.

In one embodiment, the dental handpiece 100 is devoid of potting. Being devoid of potting further permits steam, chemicals, and/or heat to pass into and out of the interior of the dental handpiece 100, allows for the heating and cooling expansion and contraction of parts of different coefficients of thermal expansion without the developing electrical short-circuits, and allows sterilization of the dental handpiece 100.

According to one embodiment, the dental handpiece 100 is assembled by an initial assembly of the inner barrel 101 with the securing mechanisms 121, for example, bearings, in the larger open end 104 and the small open end 102, and an initial assembly of the coil unit 107. The inner barrel 101 and the coil unit 107 are then secured together, for example, by being locked/snapped together.

Figure 5:
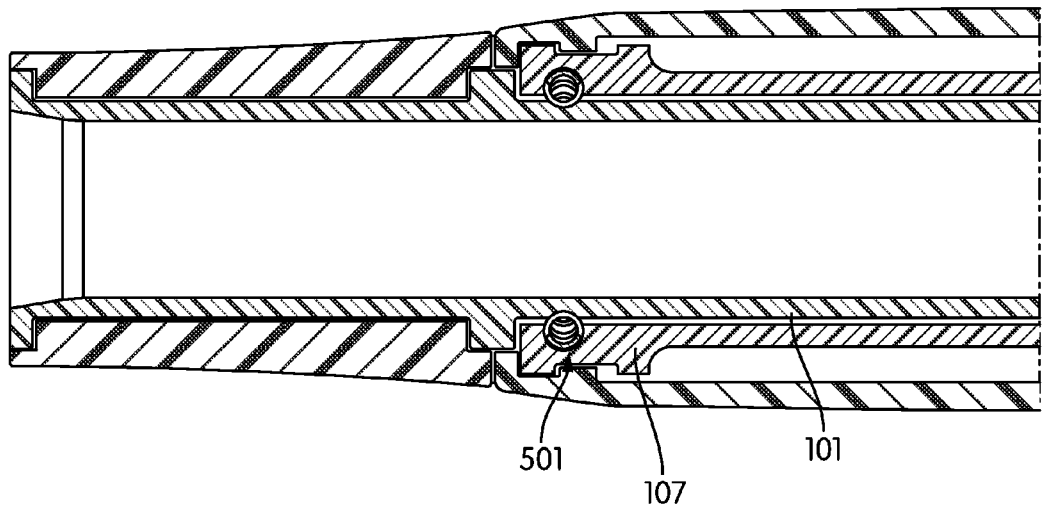
FIG. 5 is a side view of a portion of an embodiment of a dental handpiece having a canted coil spring securing a coil unit and an inner barrel, according to the disclosure.

As shown in FIG. 5, in one embodiment, the inner barrel 101 and the coil unit 107 are removably secured by a canted coil spring 501 positioned between the inner barrel 101 and the coil unit 107. In a further embodiment, a non-toxic compatible lubricant, such as food-grade silicone or teflon, is included in contact with the canted coil spring 501.

Figure 6:
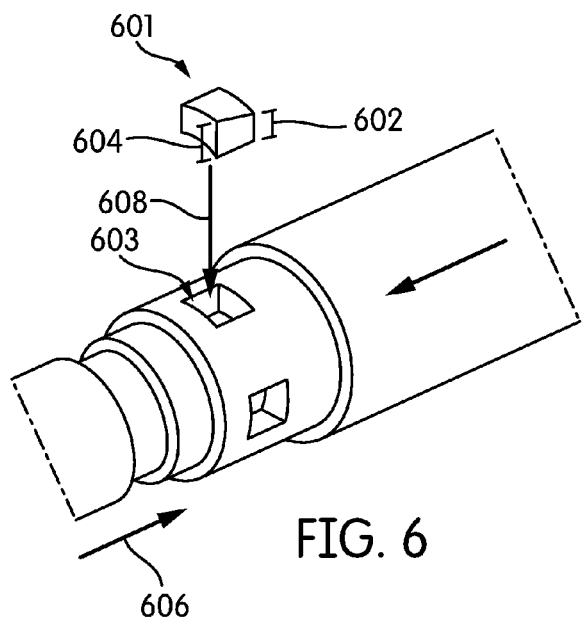
FIG. 6 is a perspective view of a portion of an embodiment of a dental handpiece having a body of increasing width to secure a coil unit and an inner barrel, according to the disclosure.

As shown in FIG. 6, according to an embodiment, one suitable technique for securing the inner barrel 101 and the coil unit 107 or for securing other elements of the dental handpiece 100 includes positioning bodies 601 having an increasing width (for example, based upon a first width 602 being smaller than a second width 604 along an insertion direction 606) into open regions 603 in a direction 608 perpendicular to the insertion direction 606 prior to insertion of the coil unit 107.

Figure 7:
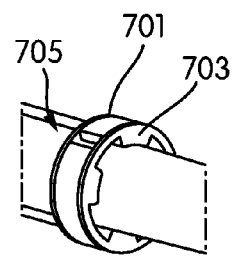
FIG. 7 is a perspective view of a portion of an embodiment of a dental handpiece having an incomplete annular structure securing a coil unit and an inner barrel, according to the disclosure.
Figure 8:
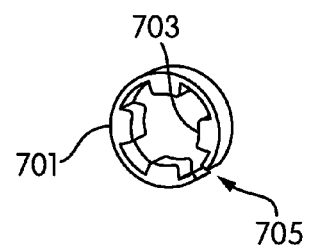
FIG. 8 is a perspective view of an incomplete annular structure for securing a coil unit and an inner barrel, according to the disclosure.

Referring to FIGS. 7 and 8, according to one embodiment, a technique for securing the inner barrel 101 and the coil unit 107 or for securing other elements of the dental handpiece 100 includes an incomplete annular structure 701 that has protruding portions 703 and is capable of compression during insertion of the coil unit 107, for example, by having a disconnected opening 705.

After securing the inner barrel 101 and the coil unit 107, the assembly of the inner barrel 101 and the coil unit 107 is inserted into the outer sheath 111, for example, such that the flanges 413 of the coil form 411 engage the interior wall of the outer sheath 111, for example, by frictionally locking. The rotatable nozzle 115 is then secured to the remaining portions of the assembly to produce the dental handpiece 100. Upon being assembled, the dental handpiece 100 is then capable of coupling and operation with a system capable of operating the dental handpiece 100. An instrument, such as, the scaler 119 is then capable of being inserted during operation of the dental handpiece 100 by the dentist or hygienists, as described above.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A dental handpiece, comprising:
   an inner barrel for rotatably retaining an ultrasonic insert, the inner barrel configured for contacting the ultrasonic insert with a cooling fluid in the inner barrel;
   a coil unit arranged and disposed to apply an alternating magnetic field to the ultrasonic insert when positioned in the inner barrel;
   an outer sheath extending around at least a portion of the coil unit;
   wherein the inner barrel is rotatable relative to at least one of the coil unit and the outer sheath;
   wherein the dental handpiece includes flow regions permitting steam, chemicals, and heat to flow into the inner barrel and out of the inner barrel during a sterilization technique.

2. The dental handpiece of claim 1, wherein the outer sheath has a first coefficient of thermal expansion and the coil unit has a second coefficient of thermal expansion, the first coefficient of thermal expansion differing from the second coefficient of thermal expansion by a value beyond a fracture value.

3. The dental handpiece of claim 1, wherein the coil unit is movably secured within the outer sheath.

4. The dental handpiece of claim 1, wherein the outer sheath extends around the inner barrel.

5. The dental handpiece of claim 1, further comprising a rotatable nozzle extending from the inner barrel and configured for rotation of the rotatable nozzle to rotate the ultrasonic insert.

6. The dental handpiece of claim 5, wherein the rotatable nozzle is rotatable 360 degrees.

7. The dental handpiece of claim 5, wherein the rotatable nozzle is selectively rotatable in response to application of a torsional load to a grip region positioned between the rotatable nozzle and the outer sheath.

8. The dental handpiece of claim 5, wherein the rotatable nozzle is capable of being locked in a fixed position.

9. The dental handpiece of claim 5, wherein the rotatable nozzle is configured for at least rotation at a first torque level and a second torque level, the first torque level being different from the second torque level.

10. The dental handpiece of claim 1, further comprising a grip region positioned between the rotatable nozzle and the outer sheath, the grip region being an elastomeric material.

11. The dental handpiece of claim 1, wherein the dental handpiece is configured to mate with a scaler.

12. The dental handpiece of claim 11, wherein the scaler is a 30 kHz magnetorestrictive scaler.

13. The dental handpiece of claim 1, further comprising one or more securing mechanisms arranged and disposed to secure the dental handpiece and permit disassembly of the dental handpiece.

14. The dental handpiece of claim 13, wherein the one or more securing mechanisms comprises a seal assembly, the seal assembly comprising one or more compliant members arranged on a seal carrier.

15. The dental handpiece of claim 14, wherein the seal carrier comprises grooves for receiving the one or more compliant members, the seal carrier and compliant members having a low friction coefficient such that the compliant members rotate over the seal carrier with little to no friction or wear.

16. The dental handpiece of claim 14, wherein the inner barrel comprises one or more receiving grooves for receiving the one or more compliant members, the receiving grooves arranged to allow the seal carrier to fit precisely in an axial position with an end of the inner barrel.

17. The dental handpiece of claim 16, wherein the seal carrier further comprises a flange portion disposed between a first pair of compliant members and grooves and a second pair of compliant members; the pair of compliant members configured to engage the receiving grooves, and the second pair of compliant members configured to extend externally of the inner barrel and flange.

18. The dental handpiece of claim 14, wherein the seal carrier comprises a compliant material.

19. A dental handpiece, comprising:
an inner barrel for rotatably retaining an ultrasonic insert, the inner barrel configured for contacting the ultrasonic insert with a cooling fluid in the inner barrel;
a coil unit arranged and disposed to apply an alternating magnetic field to the ultrasonic insert when positioned in the inner barrel; and
an outer sheath extending around at least a portion of the coil unit;
wherein the inner barrel is rotatable relative to at least one of the coil unit and the outer sheath;
wherein the dental handpiece is configured for adjusting torque from a lower torque level to a higher torque level by adjustment of a swivel drag adjustment screw.

20. A dental cleaning procedure, comprising:
operating a dental handpiece thereby applying an alternating magnetic field to an ultrasonic insert positioned in an inner barrel of the dental handpiece, the inner barrel having a first seal at a distal end and a second seal between a proximal end and the distal end; and
autoclaving the dental handpiece, allowing steam to flow through flow regions in the dental handpiece.

* * * * *